United States Patent [19]

Trapini et al.

[11] Patent Number: 4,972,832
[45] Date of Patent: Nov. 27, 1990

[54] THERMAL PACK HOLDER

[76] Inventors: Karen F. Trapini; Annette L. Trapini, both of 206 3rd St., Scotia, N.Y. 12302

[21] Appl. No.: 436,721
[22] Filed: Nov. 15, 1989
[51] Int. Cl.$^5$ ............................................. A61F 7/00
[52] U.S. Cl. ................................... 128/402; 128/82.1
[58] Field of Search ............. 128/402, 403, 399, 379, 128/380, 384, 82.1, 24.1, DIG. 15; 383/901; 62/530, 259.3; 165/46; 126/204, 263

[56] References Cited

U.S. PATENT DOCUMENTS

| 2,403,676 | 7/1946 | Modlaski | 128/402 |
| 2,710,008 | 6/1955 | Jensen | 126/204 |
| 2,842,655 | 7/1958 | Schwebel | 128/402 |
| 3,802,215 | 4/1974 | Rowe | 62/259.3 |
| 3,834,396 | 9/1974 | Foster | 128/403 |
| 3,950,789 | 4/1976 | Konz et al. | 128/402 |
| 4,382,446 | 5/1983 | Truelock | 128/403 |
| 4,556,055 | 12/1985 | Bonner, Jr. | 128/402 |
| 4,742,827 | 5/1988 | Lipton | 128/402 |
| 4,753,240 | 6/1988 | Sparks | 128/402 |

FOREIGN PATENT DOCUMENTS 1600505 10/1981 United Kingdom .

Primary Examiner—Edward M. Coven
Assistant Examiner—Mark S. Graham
Attorney, Agent, or Firm—Schmeiser, Morelle & Watts

[57] ABSTRACT

A therapeutic wrap having a plurality of pockets for selectively holding thermal packs. Straps for securing the wrap to the individual are adjacent placket apertures so that the straps may extend from either side of the wrap to allow securement when the wrap is folded to reduce its operative size.

11 Claims, 3 Drawing Sheets

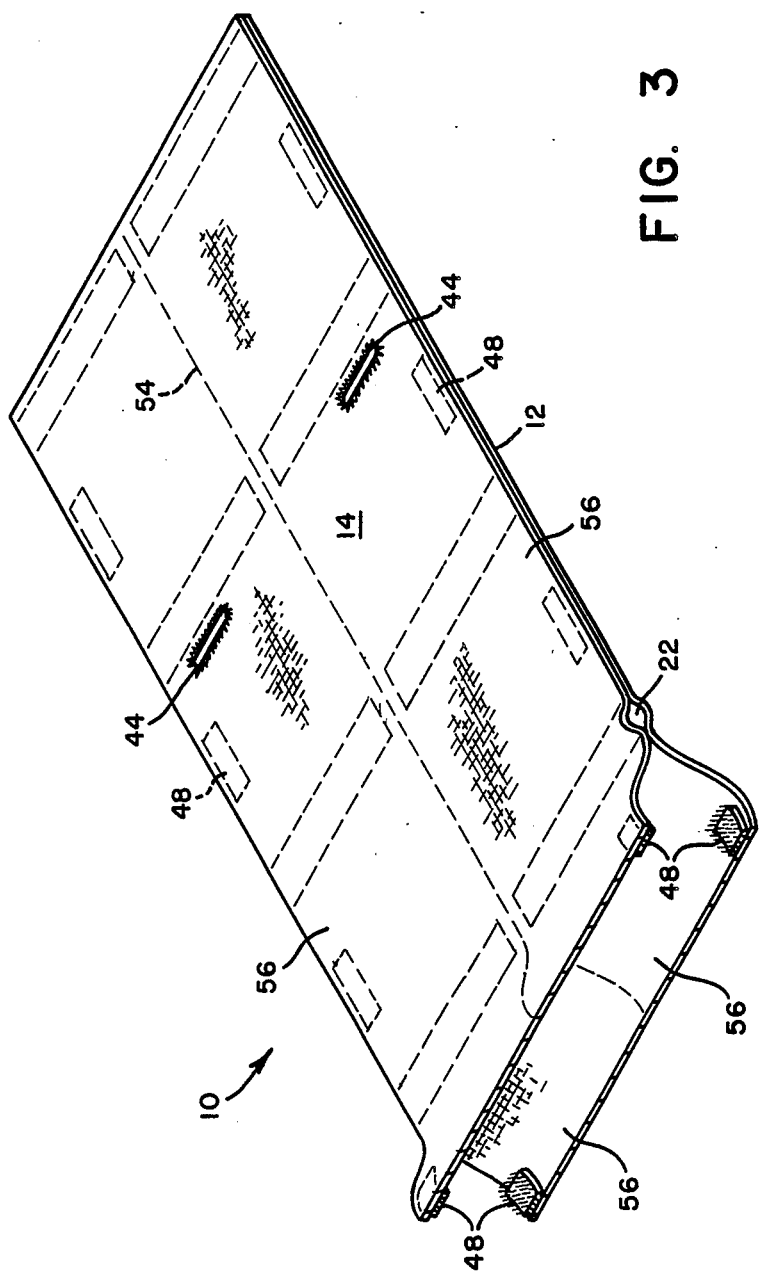

THERMAL PACK HOLDER

FIELD OF THE INVENTION

Generally, this invention relates to thermal pack holders used for treating injuries. More specifically, the invention is a multi-compartmented thermal pack holder adjustable into a variety of configurations for maximum application to the point of injury.

BACKGROUND OF THE INVENTION

Physical exercise, and, in particular, participation in athletic activities are currently very popular forms of recreation. Furthermore, physical exercise in athletic activities are entered into by young and old alike, with age being a much reduced factor in the limitation of one's activities. Thus, a wide variety of injuries have become commonplace. These injuries are treated in a variety of ways including the use of slings, immobilizing splints or fluid absorbent materials. In addition, it is common to utilize either hot packs or cold packs, hereinafter referred to as thermal packs, to alleviate pain, reduce swelling, and/or increase blood circulation to the affected body part.

These thermal packs traditionally have been held in place either by hand, or by swathes of tape or fabric wrapped around both the thermal pack and the injured body part. The former approach, depending upon the placement of the thermal pack, is either uncomfortable or else virtually impossible, while the approach is inconvenient at best, depending upon the body part to which the thermal pack is applied. The awkwardness of the swathing method becomes even more apparent as the pack shifts position or needs to be replaced by a fresh thermal pack in order to maintain the desired temperature. In such a case, the wrap material must be unwrapped and then rewrapped, which is not only time consuming but may be extremely uncomfortable where adhesive materials are used to secure the pack. Where an elastic bandage is used to secure the pack, the compounded effect of the bandage as it is wrapped around the body and thermal pack can reduce circulation, or at best becomes uncomfortable.

More recently, specialized thermal packs have been developed which have adjustable, easy to use fasteners. These thermal packs come in a variety of sizes and shapes and are configured to treat a specific injury area. For example, U.S. Pat. No. 4,628,932 is a thermal pack used solely for application to an injured knee. This invention maintains a void in the area of the knee-cap in order to prevent cold temperatures from long term contact with the patella. While the specificity of these ice packs aids in the treatment of the injuries, significant difficulties are encountered as one attempts to forecast the type of injuries to be incurred and then seeks to have a sufficient variety of thermal packs available to meet this need. This situation is especially acute in high schools and the like where funding is often limited, and it is, therefore, sometimes financially impossible to purchase a sufficient quantity of these high priced, injury specific, thermal packs to meet the needs of those injured. Furthermore, most school athletic departments and recreational sports facilities seldom have sufficient storage space to stock, and freeze a wide variety of these packs. Thus, when injuries do occur, they are often treated with rudimentary, makeshift materials which are significantly less effective. This of course prevents the most effective treatment at the onset of the injury, which is generally the most crucial time period, thus allowing the injured to worsen, and prolonging the recovery time. Furthermore, even schools which do have an array of thermal packs may find themselves without a sufficient supply due to a plurality of similar injuries each requiring the same particularly configured thermal pack.

In addition to the difficulties encountered with injury specific thermal packs, thermal pack holders are generally limited in the number and type of thermal pack compartments utilized, thereby limiting their versatility in application to the specific injury sites. Furthermore, such packs are generally held in place by straps which wrap around the user and are reattached to the thermal pack holder. The straps must generally be secured in a particular fashion which further limits the variety of applications possible with such packs. Often, even the most simple modifications of a holder requires realignments and twisting of the straps to secure the holder in place. Since these general holders are not versatile enough to obtain the required configurations, the holder is often not sufficiently secure and the awkward wrapping is such that the user is caused additional discomfort.

Because injuries can occur to large areas such as shoulders, backs and the like, as easily as they can to elbows, and other smaller areas, various size thermal pack holders are desirable. However, the inability of present devices to accommodate both large and small injury areas while at the same time conforming to the injury site for maximum heat transfer has resulted in the aforementioned proliferation of injury specific thermal packs.

The subject invention seeks to provide the versatility required to treat different sized injury areas while providing a method for securing the thermal pack holder so as to maintain sufficient contact with the injured area, with the device conforming to the injury site.

SUMMARY OF THE INVENTION

In response to these needs the subject invention was developed providing a therapeutic wrap for holding thermal packs with a great deal of versatility. One side of the thermal pack has a plurality of channels to receive thermal packs. These channels may be used selectively depending on the location and size of the injury. The opposite side of the wrap contains an enlarged pouch which is suitable for large injury areas such as shoulders, backs, thighs and the like. The wrap may also be folded lengthwise and/or widthwise in order to vary the dimensions of the wrap. This allows the device to be configured for both large and small injury areas as well as those that pose application difficulties such as necks, knees where the patella should not be in contact with the thermal packs, and ankles which are generally small and difficult to sufficiently envelop. In order to allow for the folding of the wrap without interfering with the straps a novel strap arrangement has been developed. This arrangement secures one end of the straps within the body of the wrap adjacent to the pouch at a location which is a distance from the closest end of the wrap approximately equal to 20% of the entire length of the wrap. Placket apertures adjacent to the straps allow the straps to be drawn through the wrap to extend out the other side for securing the wrap when it is folded to a smaller configuration.

Between the channels are receptacles which extend from one side of the wrap almost to the center point. These receptacles are adapted to receive stays which serve as stiffeners. By stiffening the wrap, two purposes are accomplished. The first is the easier insertion of the thermal packs into the pockets and the second is the utilization of the wrap as a brace to immobilize an injured area.

Once secured in place, the various pockets or pouches may be opened for replacement of a thermal insert in order to maintain the desired thermal application.

Thus, it becomes possible for a school or athletic organization to simply purchase a plurality of similar sized thermal packs which when combined with the subject invention become injury specific. To aid in this, the pack may be formed with instructions whereby each pouch and snap is numbered in order to easily direct the user to obtain the necessary wrap configuration.

BRIEF DESCRIPTION OF THE DRAWINGS

FIG. 3 is a perspective plan view of the side of the invention opposite that shown in FIG. 1.

DETAILED DESCRIPTION OF THE DRAWINGS

Figure 1:
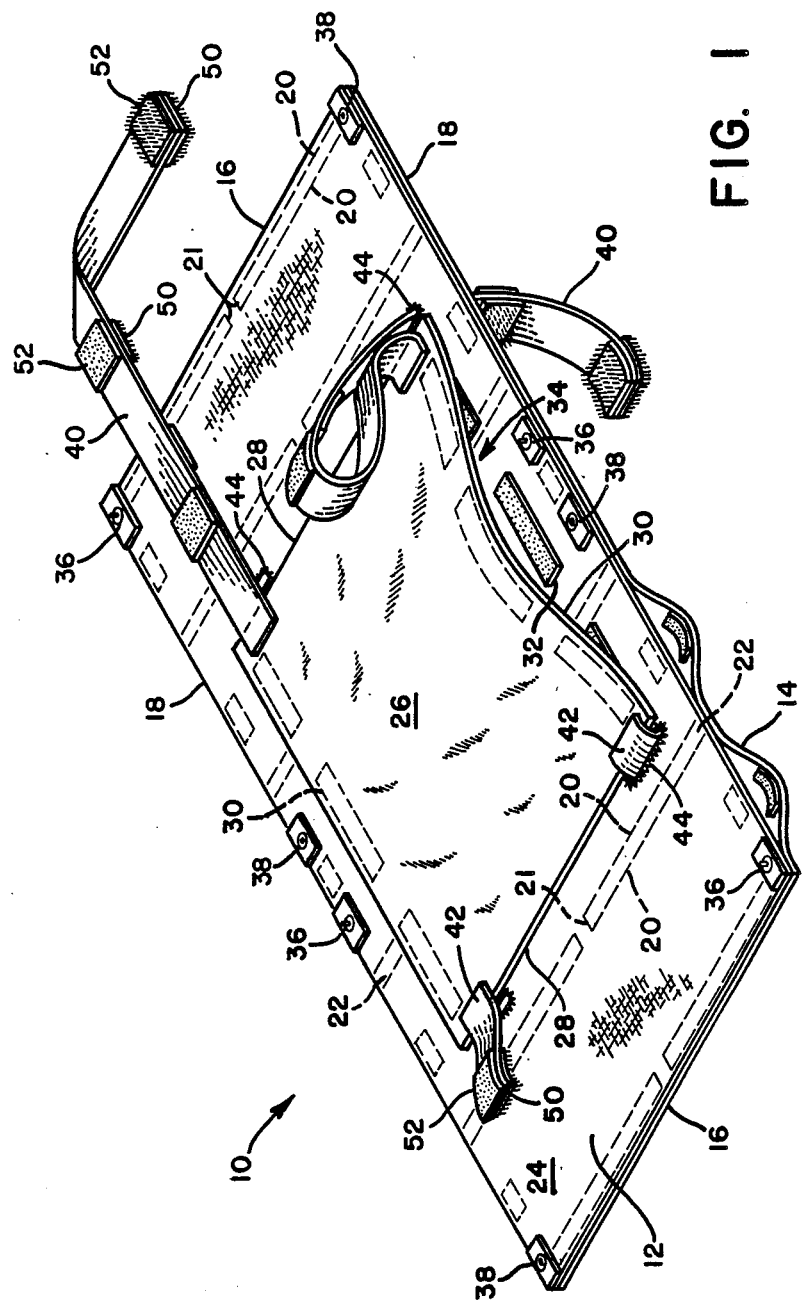
FIG. 1 is a perspective plan view of one side of the invention.

FIG. 1 discloses the therapeutic wrap generally designated as 10. The wrap has a first sheet 12 and a second sheet 14 which are secured to each other along the end edges 16. At preselected locations along the side edges 18, the first and second sheets are secured to each other by parallel stitches 20, and a base stitch 21 which form receptacles 22 for receiving stays that stiffen the wrap.

Attached to the outer surface 24 of sheet 12, is a third sheet 26, which is secured along its side edges 28 to the outer surface 24. This forms openings along both sides 30 of the third sheet 26. Fasteners 32, such as those marketed under the trademark VELCRO, allow for the closing of these openings along sides 30 to form a pouch 34 between the third sheet and the outer surface of the first sheet. Also secured to the outer surface 24, are male fasteners 36 and female fasteners 38, which interact with each other to allow the thermal wrap to be folded and secured either in half lengthwise, or with the side edges 18 either together or toward the center of the wrap.

The elongate straps 40 and short straps 42 are secured at the side edges 28 of the third sheet 26, which location is a distance from the closest side edge 18 equal to approximately 20% of the entire length of the wrap 10. Each strap is adjacent to a placket aperture 44 which extends through the wrap 10 to allow the straps to extend from either side of the wrap. Thus, there is no interference with the straps and securement to the individual even when the wrap is folded to a reduced dimension.

Figure 2:
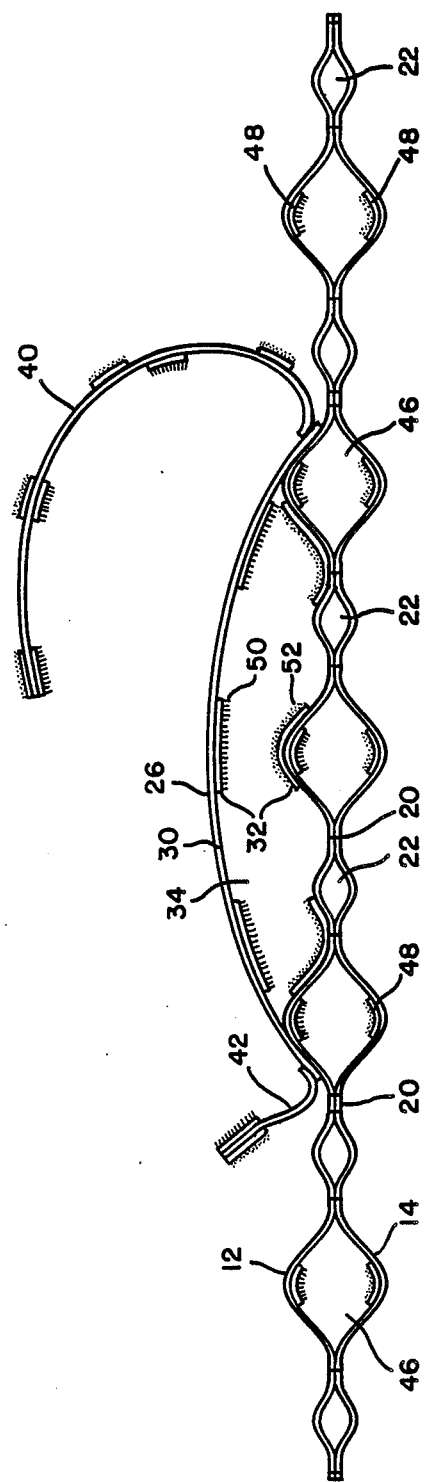
FIG. 2 is a elevational view taken along the side of the invention with a partial break away.

As shown in FIG. 2, the stitching 20 divides the wrap into a plurality of sleeves 46 which extend through the wrap from one side edge to the other for receiving thermal packs. Closure fasteners 48, such as VELCRO fasteners which have a hook portion 50 and a material portion 52, are located along the side edges 18 at the openings to the sleeves 46 for securely closing the sleeves and securing the thermal packs therein. When the wrap is folded lengthwise along center line 54 as shown in FIG. 3, the sleeves are divided in half forming pockets 56. The openings along the side edges 18 provide individual access to each pocket 56.

The elongate straps 40 contain a plurality of VELCRO type fasteners with material portions 52, opposite hook portions 50, or if preferred, material portion 52 could be adjacent to hook portions 50, which combination would be located on opposite sides of the strap for easy attachment to the short straps 42, which also have both hook portions 50 and material portions 52. Since the straps are somewhat elastic in nature, the user may vary the pressure applied by the wrap 10 to the injured area.

While the invention may be made from any one of a number of materials, in my preferred embodiment the first and third sheets are made of an elastic material such as LYCRA. This enables the user to easily insert the thermal pack which may be simply a bag of ice, even though the size of the pack is either nonuniform, or slightly larger than the pocket or pouch.

In use, the area of the injury is considered and the therapeutic wrap 10 is adjusted to obtain the proper size and configuration. This may be accomplished by referring to a chart indicating the pockets which may be numbered, should contain a thermal pack, and which snaps, color coded, should be secured to each other. Alternately a picture attached to the wrap may be used to guide the user to a particular wrap configuration and thermal pack arrangement. Thus, the wrap may be folded along center line 54 thereby reducing the width of the wrap or side edges 18 may be folded inward and secured by means of the male and female fasteners, 36 and 38 respectively. If necessary, both of these folds could be used to significantly reduce the size of the wrap. Where the wrap is reduced in size, it is necessary to insert the elongate straps 40 and short straps 42 through the placket apertures 44 so that they extend from the other side of the wrap. The wrap is then placed on the injured area and the straps 40 and 42 are secured together. Once the user is satisfied with the positioning of the wrap, thermal packs may be inserted into pockets 56 (if the wrap has been folded in half lengthwise) or else inserted into the entire length of sleeves 46 (if the wrap has not been folded in half lengthwise). In the alternative, thermal packs could be placed in pouch 34 should that be the selected area to contact the injury. After the thermal packs are inserted the pouch and/or pockets are fastened closed to secure the thermal pack therein. When it becomes necessary to remove the thermal pack and replace it one need only open the pocket or pouch, remove the used thermal pack, insert a new one and reseal said pocket or pouch.

While the above describes the preferred embodiment of the invention, it should be appreciated that many variations may be made without departing from the actual invention. For example, though not inclusive, the sides of the wrap need not be straight but could be configured with curves and the like in order to conform more exactly to certain body parts. Furthermore, other male and female fasteners could be included in order to achieve greater variation in the possible folds. For these and other reasons it is intended that the scope of the invention be limited only by the appended claims.

What is claimed:
1. A Therapeutic wrap comprising:
   a first sheet of flexible durable material having inner and outer sides and opposing side edges and ends, said side edges defining the length of the wrap and said ends defining the width of the wrap;

a second sheet of material of similar dimensions to said first sheet, said first and second sheets in registry with each other, said second sheet secured to said first sheet along outer edges of said width as well as across said width at selected locations along the side edges of the wrap, forming a plurality of open ended sleeves, each of said sleeves forming a channel between the sheets, extending from one side edge of the wrap to the other side edge, said sleeves adapted to receive removable thermal packs;

securement means for fastening the wrap to an individual, after aligning said sleeves relative to a selected body part, wherein said sleeves are held in contact with said selected body part; and a plurality of interactive fasteners located on said first sheet of material for securing said first sheet to itself for selectively reducing the dimensions of said wrap and providing a variety of size configurations.

2. The invention of claim 1 wherein said interactive fasteners further comprise a set of fasteners attached to said first sheet along and toward one of its side edges, at least one fastener located at the junction of each side edge and end; and a second set of fasteners attached along and toward the opposing side edge of said first sheet for securing said first sheet to itself when the wrap is folded toward itself, said opposing side edges securable to each other to selectively reduce the width of said wrap and dividing each of said open ended sleeves into two pockets, an end of said wrap securable at a location along the side edges for selectively reducing the length of the wrap.

3. The invention of claim 2 further comprising a plurality of receptacles constructed midpoint between adjacent pockets, said receptacles being substantially the same depth as the adjacent pockets, each of said receptacles adapted to receive a stay for stiffening the wrap.

4. The invention of claim 1 further comprising a third sheet of material attached to the outer side of said first sheet so as to form openings along opposing sides of said third sheet, forming a pouch on the outer side of said first sheet; and closure means along said openings for closing the pouch.

5. The invention of claim 1 further comprising refastenable closures at each of the open ends of said sleeves, for closing said sleeves and holding said inserts securely therein.

6. A therapeutic wrap comprising:

a first sheet of flexible durable material having inner and outer sides and opposing side edges and ends, said side edges defining the length of the wrap and said ends defining the width of the wrap;

a second sheet of material of similar dimension to said first sheet, said first and second sheets in registry with each other, said second sheet secured to said first sheet along outer edges of said width as well as across said width at selected locations along the side edges, forming a plurality of open ended sleeves, each of said sleeves forming a channel between the sheets, extending from one side edge of the wrap to the other side edge, said sleeves adapted to receive thermal inserts;

a plurality of straps secured at one end to one side of said wrap; and placket apertures extending through said wrap, each of said apertures aligned relative to a respective strap for easy insertion of the respective strap through its corresponding aperture so that each of said straps extends out of the side of the wrap opposite the side to which said straps are secured.

7. The invention of claim 6 wherein said straps are secured to the wrap at a distance from a proximal end which is approximately equal to one fifth of the entire length of the wrap.

8. The invention of claim 6 further comprising:

a third sheet of material attached to the outer side of said first sheet so as to form openings along opposing sides of said third sheet, forming a pouch on the outer side of said first sheet; and refastenable closures along said openings for closing the pouch.

9. The invention of claim 8 wherein the straps are secured to the wrap adjacent to the attachment between the outer side of the first sheet and the third sheet.

10. The invention of claim 6 further comprising refastenable closures located at the open ends of said sleeves for selectively forming pockets adapted to hold the thermal inserts.

11. The invention of claim 6 wherein said straps have a plurality of fasteners along their length for securing the straps to each other at selected locations.

* * * * *